(12) United States Patent
Kerr et al.

(10) Patent No.: US 8,454,602 B2
(45) Date of Patent: *Jun. 4, 2013

(54) APPARATUS, SYSTEM, AND METHOD FOR PERFORMING AN ELECTROSURGICAL PROCEDURE

(75) Inventors: Duane E. Kerr, Loveland, CO (US); Peter D. Gadsby, Broomfield, CO (US); Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,569

(22) Filed: May 4, 2012

(65) Prior Publication Data

US 2012/0221004 A1 Aug. 30, 2012

Related U.S. Application Data

(63) Continuation of application No. 12/437,254, filed on May 7, 2009, now Pat. No. 8,187,273.

(51) Int. Cl.
*A61B 18/18* (2006.01)

(52) U.S. Cl.
USPC .......................................................... 606/51

(58) Field of Classification Search
USPC .................... 606/50, 51, 52, 207, 210, 41, 49
See application file for complete search history.

(56) References Cited

U.S. PATENT DOCUMENTS

| 371,664 A | 10/1887 | Brannan, et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |

(Continued)

FOREIGN PATENT DOCUMENTS

| CA | 2 104 423 | 2/1994 |
| CA | 2 520 413 | 3/2007 |

(Continued)

OTHER PUBLICATIONS

U.S. Appl. No. 08/926,869, filed Sep. 10, 1997, James G. Chandler.

(Continued)

*Primary Examiner* — Kevin C Sirmons
*Assistant Examiner* — Imani Hayman

(57) ABSTRACT

The present disclosure provides a bipolar forceps. The bipolar forceps includes a housing having a handle assembly including a movable handle and one or more shafts. An end effector assembly operatively connects to a distal end of the shaft and includes a pair of first and second jaw members. A solenoid is in operative communication with the movable handle and operatively couples to a drive rod operatively coupled to at least one of the first and second jaw members for causing movement thereof. One or both of the first and second jaw members includes one or more teeth configured to engage one or more teeth located on the drive rod such that rotation of the solenoid imparts one of longitudinal and rotational movement of the drive rod such that at least one of the first and second jaw members moves between the open and closed positions.

9 Claims, 6 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,054,149 A | 9/1936 | Wappler |
| 2,113,246 A | 5/1937 | Wappler |
| 2,141,936 A | 12/1938 | Schmitt |
| 2,176,479 A | 10/1939 | Willis |
| 2,305,156 A | 4/1941 | Grubel |
| 2,245,030 A | 6/1941 | Gottesfeld et al. |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,798,688 A | 3/1974 | Wasson |
| 3,801,766 A | 4/1974 | Morrison, Jr. |
| 3,839,614 A | 10/1974 | Saganowski et al. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,031,898 A | 6/1977 | Hiltebrandt et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,102,471 A | 7/1978 | Lore et al. |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,200,105 A | 4/1980 | Gonser |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | De Medinaceli |
| 4,311,145 A | 1/1982 | Esty et al. |
| D263,020 S | 2/1982 | Rau, III |
| 4,315,510 A | 2/1982 | Kihn |
| 4,363,944 A | 12/1982 | Poirier |
| 4,370,980 A | 2/1983 | Lottick |
| 4,375,218 A | 3/1983 | Digeronimo |
| 4,394,552 A | 7/1983 | Schlosser |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,535,773 A | 8/1985 | Yoon |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,753,235 A | 6/1988 | Hasson |
| 4,754,892 A | 7/1988 | Retief |
| 4,763,669 A | 8/1988 | Jaeger |
| D298,353 S | 11/1988 | Manno |
| 4,781,175 A | 11/1988 | McGreevy et al. |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,973,801 A | 11/1990 | Frick et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,052,402 A | 10/1991 | Bencini et al. |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,144,323 A | 9/1992 | Yonkers |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,056 A | 10/1993 | Hasson |
| 5,250,063 A | 10/1993 | Abidin et al. |
| 5,254,129 A | 10/1993 | Alexander |

| Patent No. | Kind | Date | Inventor |
|---|---|---|---|
| 5,258,001 | A | 11/1993 | Corman |
| 5,258,006 | A | 11/1993 | Rydell et al. |
| 5,261,918 | A | 11/1993 | Phillips et al. |
| 5,267,998 | A | 12/1993 | Hagen |
| 5,269,780 | A | 12/1993 | Roos |
| 5,269,804 | A | 12/1993 | Bales et al. |
| D343,453 | S | 1/1994 | Noda |
| 5,275,615 | A | 1/1994 | Rose |
| 5,277,201 | A | 1/1994 | Stern |
| 5,281,220 | A | 1/1994 | Blake, III |
| 5,282,799 | A | 2/1994 | Rydell |
| 5,282,800 | A | 2/1994 | Foshee et al. |
| 5,282,826 | A | 2/1994 | Quadri |
| 5,290,286 | A | 3/1994 | Parins |
| 5,290,287 | A | 3/1994 | Boebel et al. |
| 5,300,082 | A | 4/1994 | Sharpe et al. |
| 5,304,203 | A | 4/1994 | El-Mallawany et al. |
| 5,308,353 | A | 5/1994 | Beurrier |
| 5,308,357 | A | 5/1994 | Lichtman |
| 5,312,433 | A | 5/1994 | Boebel et al. |
| 5,313,027 | A | 5/1994 | Inoue et al. |
| 5,314,445 | A | 5/1994 | Degwitz et al. |
| 5,314,463 | A | 5/1994 | Camps et al. |
| 5,318,589 | A | 6/1994 | Lichtman |
| 5,324,289 | A | 6/1994 | Eggers |
| D348,930 | S | 7/1994 | Olson |
| 5,326,806 | A | 7/1994 | Yokoshima et al. |
| 5,330,471 | A | 7/1994 | Eggers |
| 5,330,502 | A | 7/1994 | Hassler et al. |
| D349,341 | S | 8/1994 | Lichtman et al. |
| 5,334,166 | A | 8/1994 | Palestrant |
| 5,334,183 | A | 8/1994 | Wuchinich |
| 5,334,215 | A | 8/1994 | Chen |
| 5,336,220 | A | 8/1994 | Ryan et al. |
| 5,336,221 | A | 8/1994 | Anderson |
| 5,342,359 | A | 8/1994 | Rydell |
| 5,342,381 | A | 8/1994 | Tidemand |
| 5,342,393 | A | 8/1994 | Stack |
| 5,344,424 | A | 9/1994 | Roberts et al. |
| 5,350,391 | A | 9/1994 | Iacovelli |
| 5,352,222 | A | 10/1994 | Rydell |
| 5,354,271 | A | 10/1994 | Voda |
| 5,356,408 | A | 10/1994 | Rydell |
| 5,359,993 | A | 11/1994 | Slater et al. |
| 5,366,477 | A | 11/1994 | LeMarie, III et al. |
| 5,367,250 | A | 11/1994 | Whisenand |
| 5,368,600 | A | 11/1994 | Failla et al. |
| 5,374,277 | A | 12/1994 | Hassler |
| 5,376,089 | A | 12/1994 | Smith |
| 5,376,094 | A | 12/1994 | Kline |
| D354,564 | S | 1/1995 | Medema |
| 5,383,875 | A | 1/1995 | Bays et al. |
| 5,383,880 | A | 1/1995 | Hooven |
| 5,383,897 | A | 1/1995 | Wholey |
| 5,389,098 | A | 2/1995 | Tsuruta et al. |
| 5,389,103 | A | 2/1995 | Melzer et al. |
| 5,389,104 | A | 2/1995 | Hahnen et al. |
| 5,391,166 | A | 2/1995 | Eggers |
| 5,391,183 | A | 2/1995 | Janzen et al. |
| 5,395,360 | A | 3/1995 | Manoukian |
| 5,396,900 | A | 3/1995 | Slater et al. |
| 5,397,325 | A | 3/1995 | Della Badia et al. |
| 5,403,312 | A | 4/1995 | Yates et al. |
| 5,403,342 | A | 4/1995 | Tovey et al. |
| 5,405,344 | A | 4/1995 | Williamson et al. |
| 5,409,763 | A | 4/1995 | Serizawa et al. |
| D358,887 | S | 5/1995 | Feinberg |
| 5,411,519 | A | 5/1995 | Tovey et al. |
| 5,411,520 | A | 5/1995 | Nash et al. |
| 5,413,571 | A | 5/1995 | Katsaros et al. |
| 5,415,656 | A | 5/1995 | Tihon et al. |
| 5,415,657 | A | 5/1995 | Taymor-Luria |
| 5,417,709 | A | 5/1995 | Slater |
| 5,422,567 | A | 6/1995 | Matsunaga |
| 5,423,810 | A | 6/1995 | Goble et al. |
| 5,425,690 | A | 6/1995 | Chang |
| 5,425,739 | A | 6/1995 | Jessen |
| 5,429,616 | A | 7/1995 | Schaffer |
| 5,431,672 | A | 7/1995 | Cote et al. |
| 5,431,674 | A | 7/1995 | Basile et al. |
| 5,437,277 | A | 8/1995 | Dumoulin et al. |
| 5,437,292 | A | 8/1995 | Kipshidze et al. |
| 5,438,302 | A | 8/1995 | Goble |
| 5,439,478 | A | 8/1995 | Palmer |
| 5,441,517 | A | 8/1995 | Kensey et al. |
| 5,443,463 | A | 8/1995 | Stern et al. |
| 5,443,464 | A | 8/1995 | Russell et al. |
| 5,443,479 | A | 8/1995 | Bressi, Jr. |
| 5,443,480 | A | 8/1995 | Jacobs et al. |
| 5,445,638 | A | 8/1995 | Rydell et al. |
| 5,445,658 | A | 8/1995 | Durrfeld et al. |
| 5,449,480 | A | 9/1995 | Kuriya et al. |
| 5,451,224 | A | 9/1995 | Goble et al. |
| 5,454,809 | A | 10/1995 | Janssen |
| 5,454,823 | A | 10/1995 | Richardson et al. |
| 5,454,827 | A | 10/1995 | Aust et al. |
| 5,456,684 | A | 10/1995 | Schmidt et al. |
| 5,458,598 | A | 10/1995 | Feinberg et al. |
| 5,460,629 | A | 10/1995 | Shlain et al. |
| 5,461,765 | A | 10/1995 | Linden et al. |
| 5,462,546 | A | 10/1995 | Rydell |
| 5,472,442 | A | 12/1995 | Klicek |
| 5,472,443 | A | 12/1995 | Cordis et al. |
| 5,476,479 | A | 12/1995 | Green et al. |
| 5,478,351 | A | 12/1995 | Meade et al. |
| 5,480,406 | A | 1/1996 | Nolan et al. |
| 5,480,409 | A | 1/1996 | Riza |
| 5,482,054 | A | 1/1996 | Slater et al. |
| 5,484,436 | A | 1/1996 | Eggers et al. |
| 5,493,899 | A | 2/1996 | Beck et al. |
| 5,496,312 | A | 3/1996 | Klicek |
| 5,496,317 | A | 3/1996 | Goble et al. |
| 5,496,347 | A | 3/1996 | Hashiguchi et al. |
| 5,499,997 | A | 3/1996 | Sharpe et al. |
| 5,501,654 | A | 3/1996 | Failla et al. |
| 5,509,922 | A | 4/1996 | Aranyi et al. |
| 5,512,721 | A | 4/1996 | Young et al. |
| 5,514,134 | A | 5/1996 | Rydell et al. |
| 5,520,702 | A | 5/1996 | Sauer et al. |
| 5,527,313 | A | 6/1996 | Scott et al. |
| 5,528,833 | A | 6/1996 | Sakuma |
| 5,529,067 | A | 6/1996 | Larsen et al. |
| 5,531,744 | A | 7/1996 | Nardella et al. |
| 5,536,251 | A | 7/1996 | Evard et al. |
| 5,540,684 | A | 7/1996 | Hassler, Jr. |
| 5,540,685 | A | 7/1996 | Parins et al. |
| 5,540,706 | A | 7/1996 | Aust et al. |
| 5,540,715 | A | 7/1996 | Katsaros et al. |
| 5,542,945 | A | 8/1996 | Fritzsch |
| 5,549,604 | A | 8/1996 | Sutcu et al. |
| 5,554,172 | A | 9/1996 | Horner et al. |
| 5,558,671 | A | 9/1996 | Yates |
| 5,558,672 | A | 9/1996 | Edwards et al. |
| 5,562,619 | A | 10/1996 | Mirarchi et al. |
| 5,562,699 | A | 10/1996 | Heimberger et al. |
| 5,562,720 | A | 10/1996 | Stern et al. |
| 5,564,615 | A | 10/1996 | Bishop et al. |
| 5,568,859 | A | 10/1996 | Levy et al. |
| 5,569,241 | A | 10/1996 | Edwardds |
| 5,569,243 | A | 10/1996 | Kortenbach et al. |
| 5,571,100 | A | 11/1996 | Goble et al. |
| 5,573,424 | A | 11/1996 | Poppe |
| 5,573,534 | A | 11/1996 | Stone |
| 5,573,535 | A | 11/1996 | Viklund |
| 5,575,799 | A | 11/1996 | Bolanos et al. |
| 5,575,805 | A | 11/1996 | Li |
| 5,578,052 | A | 11/1996 | Koros et al. |
| 5,579,781 | A | 12/1996 | Cooke |
| 5,582,611 | A | 12/1996 | Tsukagoshi et al. |
| 5,582,617 | A | 12/1996 | Klieman et al. |
| 5,585,896 | A | 12/1996 | Yamazaki et al. |
| 5,590,570 | A | 1/1997 | LeMaire, III et al. |
| 5,591,181 | A | 1/1997 | Stone et al. |
| 5,597,107 | A | 1/1997 | Knodel et al. |
| 5,599,350 | A | 2/1997 | Schulze et al. |
| 5,601,224 | A | 2/1997 | Bishop et al. |
| 5,601,601 | A | 2/1997 | Tal et al. |
| 5,601,641 | A | 2/1997 | Stephens |

| | | | | | |
|---|---|---|---|---|---|
| 5,603,711 A | 2/1997 | Parins et al. | 5,792,177 A | 8/1998 | Kaseda |
| 5,603,723 A | 2/1997 | Aranyi et al. | 5,797,537 A | 8/1998 | Oberlin et al. |
| 5,607,436 A | 3/1997 | Pratt et al. | 5,797,927 A | 8/1998 | Yoon |
| 5,611,798 A | 3/1997 | Eggers | 5,797,938 A | 8/1998 | Paraschac et al. |
| 5,611,808 A | 3/1997 | Hossain et al. | 5,797,941 A | 8/1998 | Schulze et al. |
| 5,611,813 A | 3/1997 | Lichtman | 5,797,958 A | 8/1998 | Yoon |
| 5,618,294 A | 4/1997 | Aust et al. | 5,797,959 A | 8/1998 | Castro et al. |
| 5,618,307 A | 4/1997 | Donlon et al. | 5,800,448 A | 9/1998 | Banko |
| 5,620,415 A | 4/1997 | Lucey et al. | 5,800,449 A | 9/1998 | Wales |
| 5,620,453 A | 4/1997 | Nallakrishnan | 5,807,393 A | 9/1998 | Williamson, IV et al. |
| 5,620,459 A | 4/1997 | Lichtman | 5,810,764 A | 9/1998 | Eggers et al. |
| 5,624,452 A | 4/1997 | Yates | 5,810,805 A | 9/1998 | Sutcu et al. |
| 5,626,578 A | 5/1997 | Tihon | 5,810,808 A | 9/1998 | Eggers |
| 5,626,607 A | 5/1997 | Malecki et al. | 5,810,811 A | 9/1998 | Yates et al. |
| 5,626,609 A | 5/1997 | Zvenyatsky et al. | 5,810,877 A | 9/1998 | Roth et al. |
| 5,630,833 A | 5/1997 | Katsaros et al. | 5,814,043 A | 9/1998 | Shapeton |
| 5,637,110 A | 6/1997 | Pennybacker et al. | 5,814,054 A | 9/1998 | Kortenbach et al. |
| 5,637,111 A | 6/1997 | Sutcu et al. | 5,817,083 A | 10/1998 | Shemesh et al. |
| 5,638,003 A | 6/1997 | Hall | 5,817,119 A | 10/1998 | Klieman et al. |
| 5,638,827 A | 6/1997 | Palmer et al. | 5,820,630 A | 10/1998 | Lind |
| 5,639,403 A | 6/1997 | Ida et al. | 5,824,978 A | 10/1998 | Karasik et al. |
| 5,643,294 A | 7/1997 | Tovey et al. | 5,827,271 A | 10/1998 | Buysse et al. |
| 5,647,869 A | 7/1997 | Goble et al. | 5,827,274 A | 10/1998 | Bonnet et al. |
| 5,647,871 A | 7/1997 | Levine et al. | 5,827,279 A | 10/1998 | Hughett et al. |
| 5,649,959 A | 7/1997 | Hannam et al. | 5,827,281 A | 10/1998 | Levin |
| 5,655,650 A | 8/1997 | Naitou | 5,827,323 A | 10/1998 | Klieman et al. |
| 5,658,281 A | 8/1997 | Heard | 5,827,548 A | 10/1998 | Lavallee et al. |
| D384,413 S | 9/1997 | Zlock et al. | 5,830,212 A | 11/1998 | Cartmell et al. |
| 5,662,667 A | 9/1997 | Knodel | 5,833,690 A | 11/1998 | Yates et al. |
| 5,665,100 A | 9/1997 | Yoon | 5,833,695 A | 11/1998 | Yoon |
| 5,667,526 A | 9/1997 | Levin | 5,836,072 A | 11/1998 | Sullivan et al. |
| 5,673,841 A | 10/1997 | Schulze et al. | D402,028 S | 12/1998 | Grimm et al. |
| 5,674,220 A | 10/1997 | Fox et al. | 5,843,080 A | 12/1998 | Fleenor et al. |
| 5,674,229 A | 10/1997 | Tovey et al. | 5,849,020 A | 12/1998 | Long et al. |
| 5,681,282 A | 10/1997 | Eggers et al. | 5,849,022 A | 12/1998 | Sakashita et al. |
| 5,688,270 A | 11/1997 | Yates et al. | 5,851,214 A | 12/1998 | Larsen et al. |
| 5,690,652 A | 11/1997 | Wurster et al. | 5,853,412 A | 12/1998 | Mayenberger |
| 5,690,653 A | 11/1997 | Richardson et al. | 5,859,527 A | 1/1999 | Cook |
| 5,693,051 A | 12/1997 | Schulze et al. | 5,860,976 A | 1/1999 | Billings et al. |
| 5,693,920 A | 12/1997 | Maeda | 5,865,361 A | 2/1999 | Milliman et al. |
| 5,695,522 A | 12/1997 | LeMaire, III et al. | 5,876,401 A | 3/1999 | Schulze et al. |
| 5,700,261 A | 12/1997 | Brinkerhoff | 5,876,410 A | 3/1999 | Petillo |
| 5,700,270 A | 12/1997 | Peyser et al. | 5,876,412 A | 3/1999 | Piraka |
| 5,702,390 A | 12/1997 | Austin et al. | 5,882,567 A | 3/1999 | Cavallaro et al. |
| 5,707,369 A | 1/1998 | Vaitekunas et al. | D408,018 S | 4/1999 | McNaughton |
| 5,709,680 A | 1/1998 | Yates et al. | 5,891,141 A | 4/1999 | Rydell |
| 5,713,895 A | 2/1998 | Lontine et al. | 5,891,142 A | 4/1999 | Eggers et al. |
| 5,716,366 A | 2/1998 | Yates | 5,893,848 A | 4/1999 | Negus et al. |
| 5,720,742 A | 2/1998 | Zacharias | 5,893,863 A | 4/1999 | Yoon |
| 5,720,744 A | 2/1998 | Eggleston et al. | 5,893,875 A | 4/1999 | O'Connor et al. |
| 5,722,421 A | 3/1998 | Francese et al. | 5,893,877 A | 4/1999 | Gampp, Jr. et al. |
| 5,725,536 A | 3/1998 | Oberlin et al. | 5,897,563 A | 4/1999 | Yoon et al. |
| 5,727,428 A | 3/1998 | LeMaire, III et al. | 5,902,301 A | 5/1999 | Olig |
| 5,735,848 A | 4/1998 | Yates et al. | 5,906,630 A | 5/1999 | Anderhub et al. |
| 5,735,849 A | 4/1998 | Baden et al. | 5,907,140 A | 5/1999 | Smith |
| 5,743,906 A | 4/1998 | Parins et al. | 5,908,420 A | 6/1999 | Parins et al. |
| 5,752,973 A | 5/1998 | Kieturakis | 5,908,432 A | 6/1999 | Pan |
| 5,755,717 A | 5/1998 | Yates et al. | 5,911,719 A | 6/1999 | Eggers |
| 5,759,188 A | 6/1998 | Yoon | 5,913,874 A | 6/1999 | Berns et al. |
| 5,762,255 A | 6/1998 | Chrisman et al. | 5,921,916 A | 7/1999 | Aeikens et al. |
| 5,762,609 A | 6/1998 | Benaron et al. | 5,921,984 A | 7/1999 | Sutcu et al. |
| 5,766,130 A | 6/1998 | Selmonosky | 5,925,043 A | 7/1999 | Kumar et al. |
| 5,766,166 A | 6/1998 | Hooven | 5,928,136 A | 7/1999 | Barry |
| 5,766,170 A | 6/1998 | Eggers | 5,935,126 A | 8/1999 | Riza |
| 5,766,196 A | 6/1998 | Griffiths | 5,938,589 A | 8/1999 | Wako et al. |
| 5,769,849 A | 6/1998 | Eggers | 5,941,869 A | 8/1999 | Patterson et al. |
| 5,772,655 A | 6/1998 | Bauer et al. | 5,944,718 A | 8/1999 | Dafforn et al. |
| 5,772,670 A | 6/1998 | Brosa | 5,951,545 A | 9/1999 | Schilling et al. |
| 5,776,128 A | 7/1998 | Eggers | 5,951,546 A | 9/1999 | Lorentzen |
| 5,776,130 A | 7/1998 | Buysse et al. | 5,951,549 A | 9/1999 | Richardson et al. |
| 5,776,156 A | 7/1998 | Shikhman | 5,954,720 A | 9/1999 | Wilson et al. |
| 5,779,646 A | 7/1998 | Koblish et al. | 5,954,731 A | 9/1999 | Yoon |
| 5,779,701 A | 7/1998 | McBrayer et al. | 5,954,733 A | 9/1999 | Yoon |
| 5,779,727 A | 7/1998 | Orejola | 5,957,923 A | 9/1999 | Hahnen et al. |
| 5,781,048 A | 7/1998 | Nakao et al. | 5,957,937 A | 9/1999 | Yoon |
| H1745 H | 8/1998 | Paraschac | 5,960,544 A | 10/1999 | Beyers |
| 5,791,231 A | 8/1998 | Cohn et al. | 5,961,514 A | 10/1999 | Long et al. |
| 5,792,137 A | 8/1998 | Carr et al. | 5,964,758 A | 10/1999 | Dresden |
| 5,792,165 A | 8/1998 | Klieman et al. | 5,967,997 A | 10/1999 | Turturro et al. |

| | | |
|---|---|---|
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,993,474 A | 11/1999 | Ouchi |
| 5,997,565 A | 12/1999 | Inoue |
| 6,003,517 A | 12/1999 | Sheffield et al. |
| 6,004,332 A | 12/1999 | Yoon et al. |
| 6,004,335 A | 12/1999 | Vaitekunas et al. |
| 6,010,516 A | 1/2000 | Hulka et al. |
| 6,010,519 A | 1/2000 | Mawhirt et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,995 A | 4/2000 | Durgin |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,063,103 A | 5/2000 | Hashiguchi |
| 6,066,139 A | 5/2000 | Ryan et al. |
| 6,071,283 A | 6/2000 | Nardella et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,150 A | 7/2000 | Aznoian et al. |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,537 A | 8/2000 | Sugai et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,152,924 A | 11/2000 | Parins |
| 6,159,217 A | 12/2000 | Robie et al. |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,399 B1 | 2/2001 | Palmer et al. |
| 6,190,400 B1 | 2/2001 | Vandemoer et al. |
| 6,193,709 B1 | 2/2001 | Miyawaki et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,758 B1 | 7/2001 | Daw et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,876 B1 | 4/2002 | Erb et al. |
| 6,364,879 B1 | 4/2002 | Chen et al. |
| D457,958 S | 5/2002 | Dycus et al. |
| D457,959 S | 5/2002 | Tetzlaff et al. |
| 6,385,265 B1 | 5/2002 | Duffy et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,130 B1 | 8/2002 | Mulier et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,888 B1 | 12/2002 | Laufer et al. |
| 6,500,176 B1 | 12/2002 | Truckai et al. |

| | | |
|---|---|---|
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 | 2/2003 | Hooven et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,537,272 B2 | 3/2003 | Christopherson et al. |
| 6,540,745 B1 | 4/2003 | Fairbourn et al. |
| 6,545,239 B2 | 4/2003 | Spedale et al. |
| 6,554,844 B2 | 4/2003 | Lee et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,623,482 B2 | 9/2003 | Pendekanti et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,518 B2 | 11/2003 | Wellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,435 B2 | 8/2004 | Schulze et al. |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,784,405 B2 | 8/2004 | Flugstad et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |
| 6,830,174 B2 | 12/2004 | Hillstead et al. |
| 6,835,200 B2 | 12/2004 | Laufer et al. |
| 6,843,789 B2 | 1/2005 | Goble |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,905,497 B2 | 6/2005 | Truckai et al. |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,974,452 B1 | 12/2005 | Gille et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,989,017 B2 | 1/2006 | Howell et al. |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,001,408 B2 | 2/2006 | Knodel et al. |
| 7,011,657 B2 | 3/2006 | Truckai et al. |
| 7,025,763 B2 | 4/2006 | Karasawa et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,699 B2 | 6/2006 | Hess et al. |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |

| | | | |
|---|---|---|---|
| 7,101,373 B2 | 9/2006 | Dycus et al. |
| 7,103,947 B2 | 9/2006 | Sartor et al. |
| 7,107,124 B2 | 9/2006 | Green |
| 7,108,694 B2 | 9/2006 | Miura et al. |
| 7,112,199 B2 | 9/2006 | Cosmescu |
| 7,112,201 B2 | 9/2006 | Truckai et al. |
| D531,311 S | 10/2006 | Guerra et al. |
| 7,115,123 B2 | 10/2006 | Knowlton et al. |
| 7,115,139 B2 | 10/2006 | McClurken et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,632 B2 | 12/2006 | Prakash et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,184,820 B2 | 2/2007 | Jersey-Willuhn et al. |
| D538,932 S | 3/2007 | Malik |
| 7,189,233 B2 | 3/2007 | Truckai et al. |
| 7,195,631 B2 | 3/2007 | Dumbauld |
| D541,418 S | 4/2007 | Schechter et al. |
| 7,204,835 B2 | 4/2007 | Latterell et al. |
| 7,207,990 B2 | 4/2007 | Lands et al. |
| 7,208,005 B2 | 4/2007 | Frecker et al. |
| D541,611 S | 5/2007 | Aglassinge |
| D541,938 S | 5/2007 | Kerr et al |
| 7,211,084 B2 | 5/2007 | Goble et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelton, IV |
| 7,248,944 B2 | 7/2007 | Green |
| 7,252,667 B2 | 8/2007 | Moses et al. |
| 7,254,433 B2 | 8/2007 | Diab et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,288,103 B2 | 10/2007 | Suzuki |
| 7,291,161 B2 | 11/2007 | Hooven |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,326,202 B2 | 2/2008 | McGaffigan |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| 7,347,864 B2 | 3/2008 | Vargas |
| D567,943 S | 4/2008 | Moses et al. |
| 7,354,440 B2 | 4/2008 | Truckal et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,422,592 B2 | 9/2008 | Morley et al. |
| 7,425,835 B2 | 9/2008 | Eisele |
| 7,431,721 B2 | 10/2008 | Paton et al. |
| 7,435,249 B2 | 10/2008 | Buysse et al. |
| 7,438,714 B2 | 10/2008 | Phan |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,553,686 B2 | 6/2009 | George et al. |
| 7,569,626 B2 | 8/2009 | Truckai |
| 7,582,087 B2 | 9/2009 | Tetzlaff et al. |
| 7,588,565 B2 | 9/2009 | Marchitto et al. |
| 7,594,313 B2 | 9/2009 | Prakash et al. |
| 7,594,916 B2 | 9/2009 | Weinberg |
| 7,597,693 B2 | 10/2009 | Garrison |
| 7,621,910 B2 | 11/2009 | Sugi |
| 7,624,186 B2 | 11/2009 | Tanida |
| 7,625,370 B2 | 12/2009 | Hart et al. |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,004 B2 | 2/2010 | Long |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,727,231 B2 | 6/2010 | Swanson |
| 7,731,717 B2 | 6/2010 | Odom et al. |
| 7,736,374 B2 | 6/2010 | Vaughan et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |

| Patent No. | Date | Name |
|---|---|---|
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,839,674 B2 | 11/2010 | Lowrey et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |
| 7,896,878 B2 | 3/2011 | Johnson et al. |
| 7,898,288 B2 | 3/2011 | Wong |
| 7,900,805 B2 | 3/2011 | Shelton, IV et al. |
| 7,901,400 B2 | 3/2011 | Wham et al. |
| 7,905,380 B2 | 3/2011 | Shelton, IV et al. |
| 7,905,881 B2 | 3/2011 | Masuda et al. |
| 7,909,820 B2 | 3/2011 | Lipson et al. |
| 7,909,823 B2 | 3/2011 | Moses et al. |
| 7,909,824 B2 | 3/2011 | Masuda et al. |
| 7,918,848 B2 | 4/2011 | Lau et al. |
| 7,922,718 B2 | 4/2011 | Moses et al. |
| 7,922,742 B2 | 4/2011 | Hillstead et al. |
| 7,922,953 B2 | 4/2011 | Guerra |
| 7,931,649 B2 | 4/2011 | Couture et al. |
| 7,935,052 B2 | 5/2011 | Dumbauld |
| 7,945,332 B2 | 5/2011 | Schechter |
| 7,947,041 B2 | 5/2011 | Tetzlaff et al. |
| 7,949,407 B2 | 5/2011 | Kaplan et al. |
| 7,951,149 B2 | 5/2011 | Carlton |
| 7,951,150 B2 | 5/2011 | Johnson et al. |
| 7,955,326 B2 | 6/2011 | Paul et al. |
| 7,955,327 B2 | 6/2011 | Sartor et al. |
| 7,955,331 B2 | 6/2011 | Truckai et al. |
| 7,955,332 B2 | 6/2011 | Arts et al. |
| 7,963,965 B2 | 6/2011 | Buysse et al. |
| 7,967,839 B2 | 6/2011 | Flock et al. |
| 7,972,328 B2 | 7/2011 | Wham et al. |
| 7,972,331 B2 | 7/2011 | Hafner |
| 7,976,544 B2 | 7/2011 | McClurken et al. |
| 7,981,113 B2 | 7/2011 | Truckai et al. |
| 7,988,507 B2 | 8/2011 | Darley et al. |
| 7,998,095 B2 | 8/2011 | McAuley |
| 8,012,150 B2 | 9/2011 | Wham et al. |
| 8,016,827 B2 | 9/2011 | Chojin |
| 8,034,049 B2 | 10/2011 | Odom et al. |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |
| 8,070,748 B2 | 12/2011 | Hixson et al. |
| 8,075,580 B2 | 12/2011 | Makower |
| 8,089,417 B2 | 1/2012 | Popovic et al. |
| 8,092,451 B2 | 1/2012 | Schechter et al. |
| 8,104,956 B2 | 1/2012 | Blaha |
| 8,112,871 B2 | 2/2012 | Brandt et al. |
| 8,114,122 B2 | 2/2012 | Nau, Jr. |
| 8,123,743 B2 | 2/2012 | Arts et al. |
| 8,128,624 B2 | 3/2012 | Couture et al. |
| 8,128,625 B2 | 3/2012 | Odom |
| 8,133,224 B2 | 3/2012 | Geiselhart |
| 8,133,254 B2 | 3/2012 | Dumbauld et al. |
| 8,147,489 B2 | 4/2012 | Moses et al. |
| 2002/0107517 A1 | 8/2002 | Witt et al. |
| 2002/0111624 A1 | 8/2002 | Witt et al. |
| 2002/0165469 A1 | 11/2002 | Murakami |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto, Jr. et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0191396 A1 | 10/2003 | Sanghvi et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0176779 A1 | 9/2004 | Casutt et al. |
| 2004/0199181 A1 | 10/2004 | Knodel et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0090817 A1 | 4/2005 | Phan |
| 2005/0096645 A1 | 5/2005 | Wellman et al. |
| 2005/0149017 A1 | 7/2005 | Dycus |
| 2005/0254081 A1 | 11/2005 | Ryu et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079933 A1 | 4/2006 | Hushka et al. |
| 2006/0084973 A1 | 4/2006 | Hushka |
| 2006/0111711 A1 | 5/2006 | Goble |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0224053 A1 | 10/2006 | Black et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0271030 A1 | 11/2006 | Francis et al. |
| 2006/0283093 A1 | 12/2006 | Petrovic et al. |
| 2006/0287641 A1 | 12/2006 | Perlin |
| 2007/0027447 A1 | 2/2007 | Theroux et al. |
| 2007/0043337 A1 | 2/2007 | McAuley |
| 2007/0043353 A1 | 2/2007 | Dycus et al. |
| 2007/0062017 A1 | 3/2007 | Dycus et al. |
| 2007/0118115 A1 | 5/2007 | Artale et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0225695 A1 | 9/2007 | Mayer et al. |
| 2007/0255279 A1 | 11/2007 | Buysse et al. |
| 2007/0260238 A1 | 11/2007 | Guerra |
| 2007/0260242 A1 | 11/2007 | Dycus et al. |
| 2007/0265616 A1 | 11/2007 | Couture et al. |
| 2007/0265620 A1 | 11/2007 | Kraas et al. |
| 2008/0004616 A1 | 1/2008 | Patrick |
| 2008/0015575 A1 | 1/2008 | Odom et al. |
| 2008/0033428 A1 | 2/2008 | Artale et al. |
| 2008/0039831 A1 | 2/2008 | Odom et al. |
| 2008/0039835 A1 | 2/2008 | Johnson et al. |
| 2008/0045947 A1 | 2/2008 | Johnson et al. |
| 2008/0046122 A1 | 2/2008 | Manzo et al. |
| 2008/0058802 A1 | 3/2008 | Couture et al. |
| 2008/0082100 A1 | 4/2008 | Orton et al. |
| 2008/0125767 A1 | 5/2008 | Blaha |
| 2008/0125797 A1 | 5/2008 | Kelleher |
| 2008/0171938 A1 | 7/2008 | Masuda et al. |
| 2008/0172051 A1 | 7/2008 | Masuda et al. |
| 2008/0208289 A1 | 8/2008 | Darley et al. |

| | | |
|---|---|---|
| 2008/0215050 A1 | 9/2008 | Bakos |
| 2008/0234701 A1 | 9/2008 | Morales et al. |
| 2008/0243106 A1 | 10/2008 | Coe et al. |
| 2008/0243120 A1 | 10/2008 | Lawes et al. |
| 2008/0243158 A1 | 10/2008 | Morgan |
| 2008/0249523 A1 | 10/2008 | McPherson et al. |
| 2008/0249527 A1 | 10/2008 | Couture |
| 2008/0271360 A1 | 11/2008 | Barfield |
| 2008/0281311 A1 | 11/2008 | Dunning et al. |
| 2008/0300580 A1 | 12/2008 | Shelton, IV et al. |
| 2008/0312653 A1 | 12/2008 | Arts et al. |
| 2008/0319292 A1 | 12/2008 | Say et al. |
| 2008/0319442 A1 | 12/2008 | Unger et al. |
| 2009/0012520 A1 | 1/2009 | Hixson et al. |
| 2009/0012556 A1 | 1/2009 | Boudreaux et al. |
| 2009/0015832 A1 | 1/2009 | Popovic et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0054894 A1 | 2/2009 | Yachi |
| 2009/0062794 A1 | 3/2009 | Buysse et al. |
| 2009/0065565 A1 | 3/2009 | Cao |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0105750 A1 | 4/2009 | Price et al. |
| 2009/0112200 A1 | 4/2009 | Eggers |
| 2009/0112206 A1 | 4/2009 | Dumbauld et al. |
| 2009/0112229 A1 | 4/2009 | Omori et al. |
| 2009/0131934 A1 | 5/2009 | Odom et al. |
| 2009/0138006 A1 | 5/2009 | Bales et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171354 A1 | 7/2009 | Deville et al. |
| 2009/0177094 A1 | 7/2009 | Brown et al. |
| 2009/0182327 A1 | 7/2009 | Unger |
| 2009/0182329 A1 | 7/2009 | Dycus |
| 2009/0187188 A1 | 7/2009 | Guerra et al. |
| 2009/0198233 A1 | 8/2009 | Chojin |
| 2009/0204114 A1 | 8/2009 | Odom |
| 2009/0204137 A1 | 8/2009 | Maxwell |
| 2009/0206126 A1 | 8/2009 | Huitema et al. |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248007 A1 | 10/2009 | Falkenstein et al. |
| 2009/0248013 A1 | 10/2009 | Falkenstein et al. |
| 2009/0248019 A1 | 10/2009 | Falkenstein et al. |
| 2009/0248020 A1 | 10/2009 | Falkenstein et al. |
| 2009/0248021 A1 | 10/2009 | McKenna |
| 2009/0248022 A1 | 10/2009 | Falkenstein et al. |
| 2009/0248050 A1 | 10/2009 | Hirai |
| 2009/0248051 A1 | 10/2009 | Masuda |
| 2009/0254080 A1 | 10/2009 | Honda |
| 2009/0254081 A1 | 10/2009 | Allison et al. |
| 2009/0261804 A1 | 10/2009 | McKenna et al. |
| 2009/0270771 A1 | 10/2009 | Takahashi |
| 2009/0292282 A9 | 11/2009 | Dye |
| 2009/0318912 A1 | 12/2009 | Mayer et al. |
| 2010/0016857 A1 | 1/2010 | McKenna et al. |
| 2010/0023009 A1 | 1/2010 | Moses et al. |
| 2010/0030028 A1 | 2/2010 | Cabrera et al. |
| 2010/0036375 A1 | 2/2010 | Regadas |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton et al. |
| 2010/0049194 A1 | 2/2010 | Hart et al. |
| 2010/0057078 A1 | 3/2010 | Arts et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0087818 A1 | 4/2010 | Cunningham |
| 2010/0094271 A1 | 4/2010 | Ward et al. |
| 2010/0094286 A1 | 4/2010 | Chojin |
| 2010/0094287 A1 | 4/2010 | Cunningham et al. |
| 2010/0094289 A1 | 4/2010 | Taylor et al. |
| 2010/0100122 A1 | 4/2010 | Hinton |
| 2010/0130971 A1 | 5/2010 | Baily |
| 2010/0130977 A1 | 5/2010 | Garrison et al. |
| 2010/0145334 A1 | 6/2010 | Olson et al. |
| 2010/0179539 A1 | 7/2010 | Nau, Jr. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0198215 A1 | 8/2010 | Julian et al. |
| 2010/0198218 A1 | 8/2010 | Manzo |
| 2010/0198248 A1 | 8/2010 | Vakharia |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0217264 A1 | 8/2010 | Odom et al. |
| 2010/0228249 A1 | 9/2010 | Mohr et al. |
| 2010/0228250 A1 | 9/2010 | Brogna |
| 2010/0249769 A1 | 9/2010 | Nau, Jr. et al. |
| 2010/0249776 A1 | 9/2010 | Kerr |
| 2010/0256635 A1 | 10/2010 | McKenna et al. |
| 2010/0274160 A1 | 10/2010 | Yachi et al. |
| 2010/0274244 A1 | 10/2010 | Heard |
| 2010/0274265 A1 | 10/2010 | Wingardner et al. |
| 2010/0280511 A1 | 11/2010 | Rachlin et al. |
| 2010/0280515 A1 | 11/2010 | Hixson et al. |
| 2010/0286691 A1 | 11/2010 | Kerr et al. |
| 2010/0292691 A1 | 11/2010 | Brogna |
| 2010/0307934 A1 | 12/2010 | Chowaniec et al. |
| 2010/0312235 A1 | 12/2010 | Bahney |
| 2010/0312238 A1 | 12/2010 | Schechter et al. |
| 2010/0312242 A1 | 12/2010 | Odom |
| 2010/0331742 A1 | 12/2010 | Masuda |
| 2010/0331839 A1 | 12/2010 | Schechter et al. |
| 2011/0004209 A1 | 1/2011 | Lawes et al. |
| 2011/0004210 A1 | 1/2011 | Johnson et al. |
| 2011/0009864 A1 | 1/2011 | Bucciaglia et al. |
| 2011/0015632 A1 | 1/2011 | Artale |
| 2011/0018164 A1 | 1/2011 | Sartor et al. |
| 2011/0034918 A1 | 2/2011 | Reschke |
| 2011/0036183 A1 | 2/2011 | Artale et al. |
| 2011/0046623 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0060356 A1 | 3/2011 | Reschke et al. |
| 2011/0066174 A1 | 3/2011 | Gilbert |
| 2011/0071522 A1 | 3/2011 | Dumbauld et al. |
| 2011/0071523 A1 | 3/2011 | Dickhans |

| | | | | | |
|---|---|---|---|---|---|
| 2011/0071525 A1 | 3/2011 | Dumbauld et al. | DE | 29616210 | 1/1997 |
| 2011/0072638 A1 | 3/2011 | Brandt et al. | DE | 19608716 | 4/1997 |
| 2011/0073246 A1 | 3/2011 | Brandt et al. | DE | 19751106 | 5/1998 |
| 2011/0073594 A1 | 3/2011 | Bonn | DE | 19751108 | 5/1999 |
| 2011/0077648 A1 | 3/2011 | Lee et al. | DE | 19946527 | 12/2001 |
| 2011/0077649 A1 | 3/2011 | Kingsley | DE | 10045375 | 4/2002 |
| 2011/0082457 A1 | 4/2011 | Kerr et al. | DE | 10 2004 02617 | 12/2005 |
| 2011/0082494 A1 | 4/2011 | Kerr et al. | DE | 20 2007 00916 | 10/2007 |
| 2011/0087221 A1 | 4/2011 | Siebrecht et al. | DE | 20 2007 00931 | 10/2007 |
| 2011/0098689 A1 | 4/2011 | Nau, Jr. et al. | DE | 20 2007 01623 | 3/2008 |
| 2011/0106079 A1 | 5/2011 | Garrison et al. | DE | 19738457 | 1/2009 |
| 2011/0118736 A1 | 5/2011 | Harper et al. | DE | 10 2008 01840 | 7/2009 |
| 2011/0162796 A1 | 7/2011 | Guerra | EP | 0364216 | 4/1990 |
| 2011/0178519 A1 | 7/2011 | Couture et al. | EP | 0467501 | 1/1992 |
| 2011/0184405 A1 | 7/2011 | Mueller | EP | 0509670 | 10/1992 |
| 2011/0190653 A1 | 8/2011 | Harper et al. | EP | 0518230 | 12/1992 |
| 2011/0190765 A1 | 8/2011 | Chojin | EP | 0541930 | 5/1993 |
| 2011/0193608 A1 | 8/2011 | Krapohl | EP | 0306123 | 8/1993 |
| 2011/0218530 A1 | 9/2011 | Reschke | EP | 0572131 | 12/1993 |
| 2011/0230880 A1 | 9/2011 | Chojin et al. | EP | 0584787 | 3/1994 |
| 2011/0238066 A1 | 9/2011 | Olson | EP | 0589453 | 3/1994 |
| 2011/0238067 A1 | 9/2011 | Moses et al. | EP | 0589555 | 3/1994 |
| 2011/0251605 A1 | 10/2011 | Hoarau et al. | EP | 0623316 | 11/1994 |
| 2011/0251606 A1 | 10/2011 | Kerr | EP | 0624348 | 11/1994 |
| 2011/0251611 A1 | 10/2011 | Horner et al. | EP | 0640317 | 3/1995 |
| 2011/0270245 A1 | 11/2011 | Horner et al. | EP | 0648475 | 4/1995 |
| 2011/0270250 A1 | 11/2011 | Horner et al. | EP | 0650701 | 5/1995 |
| 2011/0270251 A1 | 11/2011 | Horner et al. | EP | 0694290 | 3/1996 |
| 2011/0270252 A1 | 11/2011 | Horner et al. | EP | 0717966 | 6/1996 |
| 2011/0276048 A1 | 11/2011 | Kerr et al. | EP | 0754437 | 3/1997 |
| 2011/0276049 A1 | 11/2011 | Gerhardt | EP | 0517243 | 9/1997 |
| 2011/0295251 A1 | 12/2011 | Garrison | EP | 0853922 | 7/1998 |
| 2011/0295313 A1 | 12/2011 | Kerr | EP | 0875209 | 11/1998 |
| 2011/0301592 A1 | 12/2011 | Kerr et al. | EP | 0878169 | 11/1998 |
| 2011/0301599 A1 | 12/2011 | Roy et al. | EP | 0887046 | 1/1999 |
| 2011/0301600 A1 | 12/2011 | Garrison et al. | EP | 0888747 | 1/1999 |
| 2011/0301601 A1 | 12/2011 | Garrison et al. | EP | 0913126 | 5/1999 |
| 2011/0301602 A1 | 12/2011 | Roy et al. | EP | 0923907 | 6/1999 |
| 2011/0301603 A1 | 12/2011 | Kerr et al. | EP | 0950378 | 10/1999 |
| 2011/0301604 A1 | 12/2011 | Horner et al. | EP | 0986990 | 3/2000 |
| 2011/0301605 A1 | 12/2011 | Horner | EP | 1034747 | 9/2000 |
| 2011/0301606 A1 | 12/2011 | Kerr | EP | 1034748 | 9/2000 |
| 2011/0301637 A1 | 12/2011 | Kerr et al. | EP | 1025807 | 10/2000 |
| 2011/0319886 A1 | 12/2011 | Chojin et al. | EP | 1034746 | 10/2000 |
| 2011/0319888 A1 | 12/2011 | Mueller et al. | EP | 1050278 | 11/2000 |
| 2012/0004658 A1 | 1/2012 | Chojin | EP | 1053719 | 11/2000 |
| 2012/0010614 A1 | 1/2012 | Couture | EP | 1053720 | 11/2000 |
| 2012/0022532 A1 | 1/2012 | Garrison | EP | 1055399 | 11/2000 |
| 2012/0029515 A1 | 2/2012 | Couture | EP | 1055400 | 11/2000 |
| 2012/0041438 A1 | 2/2012 | Nau, Jr. et al. | EP | 1080694 | 3/2001 |
| 2012/0046659 A1 | 2/2012 | Mueller | EP | 1082944 | 3/2001 |
| 2012/0046660 A1 | 2/2012 | Nau, Jr. | EP | 1159926 | 12/2001 |
| 2012/0046662 A1 | 2/2012 | Gilbert | EP | 1177771 | 2/2002 |
| 2012/0059371 A1 | 3/2012 | Anderson et al. | EP | 1278007 | 1/2003 |
| 2012/0059372 A1 | 3/2012 | Johnson | EP | 1301135 | 4/2003 |
| 2012/0059374 A1 | 3/2012 | Johnson et al. | EP | 1330991 | 7/2003 |
| 2012/0059375 A1 | 3/2012 | Couture et al. | EP | 1486177 | 6/2004 |
| 2012/0059408 A1 | 3/2012 | Mueller | EP | 1472984 | 11/2004 |
| 2012/0059409 A1 | 3/2012 | Reschke et al. | EP | 0774232 | 1/2005 |
| 2012/0078250 A1 | 3/2012 | Orton et al. | EP | 1527747 | 5/2005 |
| 2012/0083785 A1 | 4/2012 | Roy et al. | EP | 1530952 | 5/2005 |
| 2012/0083786 A1 | 4/2012 | Artale et al. | EP | 1532932 | 5/2005 |
| 2012/0083827 A1 | 4/2012 | Artale et al. | EP | 1535581 | 6/2005 |
| 2012/0095456 A1 | 4/2012 | Schechter et al. | EP | 1609430 | 12/2005 |
| 2012/0095460 A1 | 4/2012 | Rooks et al. | EP | 1201192 | 2/2006 |
| | | | EP | 1632192 | 3/2006 |
| FOREIGN PATENT DOCUMENTS | | | EP | 1186274 | 4/2006 |
| CA | 2 590 520 | 11/2007 | EP | 1642543 | 4/2006 |
| CN | 201299462 | 9/2009 | EP | 1645238 | 4/2006 |
| DE | 2415263 | 10/1975 | EP | 1645240 | 4/2006 |
| DE | 2514501 | 10/1976 | EP | 1649821 | 4/2006 |
| DE | 2627679 | 1/1977 | EP | 1707143 | 10/2006 |
| DE | 3423356 | 1/1986 | EP | 1545360 | 3/2007 |
| DE | 3612646 | 4/1987 | EP | 1767163 | 3/2007 |
| DE | 8712328 | 3/1988 | EP | 1769765 | 4/2007 |
| DE | 4303882 | 8/1994 | EP | 1769766 | 4/2007 |
| DE | 4403252 | 8/1995 | EP | 1772109 | 4/2007 |
| DE | 19515914 | 7/1996 | EP | 1785097 | 5/2007 |
| DE | 19506363 | 8/1996 | EP | 1785098 | 5/2007 |

| | | | | | |
|---|---|---|---|---|---|
| EP | 1785101 | 5/2007 | WO | WO 95/20921 | 8/1995 |
| EP | 1787597 | 5/2007 | WO | WO 96/05776 | 2/1996 |
| EP | 1810625 | 7/2007 | WO | WO 96/11635 | 4/1996 |
| EP | 1810628 | 7/2007 | WO | WO 96/22056 | 7/1996 |
| EP | 1842500 | 10/2007 | WO | WO 96/13218 | 9/1996 |
| EP | 1878400 | 1/2008 | WO | WO 97/00646 | 1/1997 |
| EP | 1894535 | 3/2008 | WO | WO 97/00647 | 1/1997 |
| EP | 1929970 | 6/2008 | WO | WO 97/10764 | 3/1997 |
| EP | 1946715 | 7/2008 | WO | WO 97/18768 | 5/1997 |
| EP | 1958583 | 8/2008 | WO | WO 97/24073 | 7/1997 |
| EP | 1990019 | 11/2008 | WO | WO 97/24993 | 7/1997 |
| EP | 1683496 | 12/2008 | WO | WO 98/14124 | 4/1998 |
| EP | 1997438 | 12/2008 | WO | WO 98/27880 | 7/1998 |
| EP | 1997439 | 12/2008 | WO | WO 98/31290 | 7/1998 |
| EP | 1527744 | 2/2009 | WO | WO 98/43264 | 10/1998 |
| EP | 2103268 | 9/2009 | WO | WO 99/03407 | 1/1999 |
| EP | 2105104 | 9/2009 | WO | WO 99/03408 | 1/1999 |
| EP | 2147649 | 1/2010 | WO | WO 99/03409 | 1/1999 |
| EP | 2153791 | 2/2010 | WO | WO 99/03414 | 1/1999 |
| EP | 2206474 | 7/2010 | WO | WO 99/12488 | 3/1999 |
| EP | 1920725 | 10/2010 | WO | WO 99/23933 | 5/1999 |
| EP | 2243439 | 10/2010 | WO | WO 99/23959 | 5/1999 |
| EP | 2294998 | 3/2011 | WO | WO 99/025261 | 5/1999 |
| EP | 2301467 | 3/2011 | WO | WO 99/40857 | 8/1999 |
| EP | 1628586 | 7/2011 | WO | WO 99/40485 | 8/1999 |
| GB | 623316 | 5/1949 | WO | WO 99/51158 | 10/1999 |
| GB | 1490585 | 11/1977 | WO | WO 99/66850 | 12/1999 |
| GB | 2214430 A | 6/1989 | WO | WO 00/24322 | 5/2000 |
| GB | 2213416 A | 8/1989 | WO | WO 00/24330 | 5/2000 |
| JP | 61-501068 | 9/1984 | WO | WO 00/24331 | 5/2000 |
| JP | 6-502328 | 3/1992 | WO | WO 00/33753 | 6/2000 |
| JP | 5-5106 | 1/1993 | WO | WO 00/36986 | 6/2000 |
| JP | 5-40112 | 2/1993 | WO | WO 00/41638 | 7/2000 |
| JP | 6-030945 | 2/1994 | WO | WO 00/47124 | 8/2000 |
| JP | 6-121797 | 5/1994 | WO | WO 00/53112 | 9/2000 |
| JP | 6-285078 | 10/1994 | WO | WO 00/59392 | 10/2000 |
| JP | 6-343644 | 12/1994 | WO | WO 01/01847 | 1/2001 |
| JP | 6-511401 | 12/1994 | WO | WO 01/15614 | 3/2001 |
| JP | 7-265328 | 10/1995 | WO | WO 01/17448 | 3/2001 |
| JP | 8-56955 | 3/1996 | WO | WO 01/54604 | 8/2001 |
| JP | 8-317936 | 3/1996 | WO | WO 01/66025 | 9/2001 |
| JP | 8-289895 | 5/1996 | WO | WO 02/07627 | 1/2002 |
| JP | 8-252263 | 10/1996 | WO | WO 02/058544 | 8/2002 |
| JP | 8-317934 | 12/1996 | WO | WO 02/067798 | 9/2002 |
| JP | 9-10223 | 1/1997 | WO | WO 02/080783 | 10/2002 |
| JP | 9-122138 | 5/1997 | WO | WO 02/080784 | 10/2002 |
| JP | 10-24051 | 1/1998 | WO | WO 02/080785 | 10/2002 |
| JP | 11-070124 | 5/1998 | WO | WO 02/080786 | 10/2002 |
| JP | 10-155798 | 6/1998 | WO | WO 02/080793 | 10/2002 |
| JP | 2000-102545 | 9/1998 | WO | WO 02/080794 | 10/2002 |
| JP | 11-47150 | 2/1999 | WO | WO 02/080795 | 10/2002 |
| JP | 11-169381 | 6/1999 | WO | WO 02/080796 | 10/2002 |
| JP | 11-192238 | 7/1999 | WO | WO 02/080797 | 10/2002 |
| JP | 11-244298 | 9/1999 | WO | WO 02/080798 | 10/2002 |
| JP | 2000-342599 | 12/2000 | WO | WO 02/080799 | 10/2002 |
| JP | 2000-350732 | 12/2000 | WO | WO 02/081170 | 10/2002 |
| JP | 2001-8944 | 1/2001 | WO | WO 02/085218 | 10/2002 |
| JP | 2001-29356 | 2/2001 | WO | WO 03/061500 | 7/2003 |
| JP | 2001-128990 | 5/2001 | WO | WO 03/068046 | 8/2003 |
| JP | 2001-190564 | 7/2001 | WO | WO 03/090630 | 11/2003 |
| JP | 2001-3400 | 11/2001 | WO | WO 03/096880 | 11/2003 |
| JP | 2002-528166 | 3/2002 | WO | WO 03/101311 | 12/2003 |
| JP | 2003-245285 | 9/2003 | WO | WO 2004/028585 | 4/2004 |
| JP | 2004-517668 | 6/2004 | WO | WO 2004/032776 | 4/2004 |
| JP | 2004-528869 | 9/2004 | WO | WO 2004/032777 | 4/2004 |
| JP | 2011-125195 | 6/2011 | WO | WO 2004/052221 | 6/2004 |
| SU | 401367 | 11/1974 | WO | WO 2004/073488 | 9/2004 |
| WO | WO 89/00757 | 1/1989 | WO | WO 2004/073490 | 9/2004 |
| WO | WO 92/04873 | 4/1992 | WO | WO 2004/073753 | 9/2004 |
| WO | WO 92/06642 | 4/1992 | WO | WO 2004/082495 | 9/2004 |
| WO | WO 93/19681 | 10/1993 | WO | WO 2004/098383 | 11/2004 |
| WO | WO 93/21845 | 11/1993 | WO | WO 2004/103156 | 12/2004 |
| WO | WO 94/00059 | 1/1994 | WO | WO 2005/004734 | 1/2005 |
| WO | WO 94/08524 | 4/1994 | WO | WO 2005/004735 | 1/2005 |
| WO | WO 94/20025 | 9/1994 | WO | WO 2005/009255 | 2/2005 |
| WO | WO 95/02369 | 1/1995 | WO | WO 2005/011049 | 2/2005 |
| WO | WO 95/07662 | 3/1995 | WO | WO 2005/030071 | 4/2005 |
| WO | WO 95/15124 | 6/1995 | WO | WO 2005/048809 | 6/2005 |
| WO | WO 95/20360 | 8/1995 | WO | WO 2005/050151 | 6/2005 |

| | | |
|---|---|---|
| WO | WO 2005/110264 | 11/2005 |
| WO | WO 2006/021269 | 3/2006 |
| WO | WO 2008/008457 | 1/2008 |
| WO | WO 2008/040483 | 4/2008 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |
| WO | WO 2009/032623 | 3/2009 |
| WO | WO 2009/039179 | 3/2009 |
| WO | WO 2009/039510 | 3/2009 |
| WO | WO 2009/124097 | 10/2009 |
| WO | WO 2010/104753 | 9/2010 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,091, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hernorrhoidectonny" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended-EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.

Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

APPARATUS, SYSTEM, AND METHOD FOR PERFORMING AN ELECTROSURGICAL PROCEDURE

CROSS-REFERENCE TO RELATED APPLICATIONS

The present application is a continuation of and claims the benefit of and priority to U.S. patent application Ser. No. 12/437,254 (U.S. Patent Publication No. 2010/0286691) filed on May 7, 2009 by Kerr et al. The entire contents of which incorporated herein by reference.

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an endoscopic or laparoscopic electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps or laparoscopic forceps) for remotely accessing organs through smaller, puncture-like incisions. As a direct result thereof, patients tend to benefit from less scarring and reduced healing time. Typically, the endoscopic forceps are inserted into the patient through one or more various types of cannulas or access ports (typically having an opening that ranges from about five millimeters to about twelve millimeters) that has been made with a trocar; as can be appreciated, smaller cannulas are usually preferred.

Forceps that are configured for use with small cannulas (e.g., cannulas less than five millimeters) may present design challenges for a manufacturer of surgical instruments.

SUMMARY

As noted above, smaller cannulas or access ports are usually preferred during an endoscopic procedure. However, because of size constraints associated with the cannula or access port, endoscopic forceps that are configured for use with the smaller cannulas may present design challenges for a manufacturer (e.g., designing an end effector assembly of an endoscopic forceps without compromising the integrity and/or functionality thereof).

Therefore, it may prove useful in the relevant arts to provide an endoscopic forceps that includes an end effector assembly that is configured for use with various types of cannulas or access ports including those that are less than five millimeters. With this purpose in mind, the present disclosure provides a bipolar forceps adapted to connect to a source of electrosurgical energy. The bipolar forceps includes a housing having a handle assembly including a movable handle and one or more shafts that extend from the housing that defines a longitudinal axis therethrough. An end effector assembly operatively connects to a distal end of the shaft and includes a pair of first and second jaw members movable from an open spaced apart position to a closed position to grasp tissue. A solenoid is in operative communication with the movable handle and operatively couples to a drive rod that operatively couples to at least one of the first and second jaw members for causing movement thereof. One or both of the first and second jaw members includes one or more teeth configured to engage one or more teeth located on the drive rod such that rotation of the solenoid imparts at least one of longitudinal and rotational movement of the drive rod such that at least one of the first and second jaw members moves from a first position to a second to clamp tissue.

The present disclosure also provides a method for performing an electrosurgical procedure. The method includes the initial step of providing a bipolar forceps adapted to connect to a source of electrosurgical energy. The bipolar forceps includes a housing having a handle assembly including a movable handle and one or more shafts that extend from the housing that defines a longitudinal axis therethrough. An end effector assembly operatively connects to a distal end of the shaft and includes a pair of first and second jaw members movable from an open spaced apart position to a closed position to grasp tissue. A solenoid is in operative communication with the movable handle and operatively couples to a drive rod that operatively couples to at least one of the first and second jaw members for causing movement thereof. One or both of the first and second jaw members includes one or more teeth configured to engage one or more teeth located on the drive rod such that rotation of the solenoid imparts at least one of longitudinal and rotational movement of the drive rod such that at least one of the first and second jaw members moves from a first position to a second to clamp tissue. The method also includes the steps of: positioning tissue between the pair of first and second jaw members; actuating the electromechanical device to move the drive rod causing the first and second jaw members to move towards each other such that tissue is grasped therebetween; and applying electrosurgical energy to the jaw members such that a tissue seal may be effected therebetween.

The present disclosure further provides a system for performing an electrosurgical device. The system includes a bipolar forceps adapted to connect to a source of electrosurgical energy. The bipolar forceps includes a housing having a handle assembly including a movable handle and one or more shafts that extend from the housing that defines a longitudinal axis therethrough. An end effector assembly operatively connects to a distal end of the shaft and includes a pair of first and second jaw members movable from an open spaced apart position to a closed position to grasp tissue. A solenoid is in operative communication with the movable handle and operatively couples to a drive rod that operatively couples to at least one of the first and second jaw members for causing movement thereof. One or both of the first and second jaw members includes one or more teeth configured to engage one or more teeth located on the drive rod such that rotation of the solenoid imparts at least one of longitudinal and rotational movement of the drive rod such that at least one of the first and second jaw members moves from a first position to a second to clamp tissue. The system also includes a control system having one or more algorithms for one of independently controlling and monitoring the delivery of electrosurgical energy from the source of electrosurgical energy to the electromechanical device and a tissue sealing plate on each of the jaw members.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present disclosure includes an electrosurgical apparatus (e.g., endoscopic or laparoscopic forceps) that includes an end effector assembly that includes a jaw assembly operatively coupled to one or more electromechanical drive assemblies for causing movement of the jaw assembly.

Figure 1:
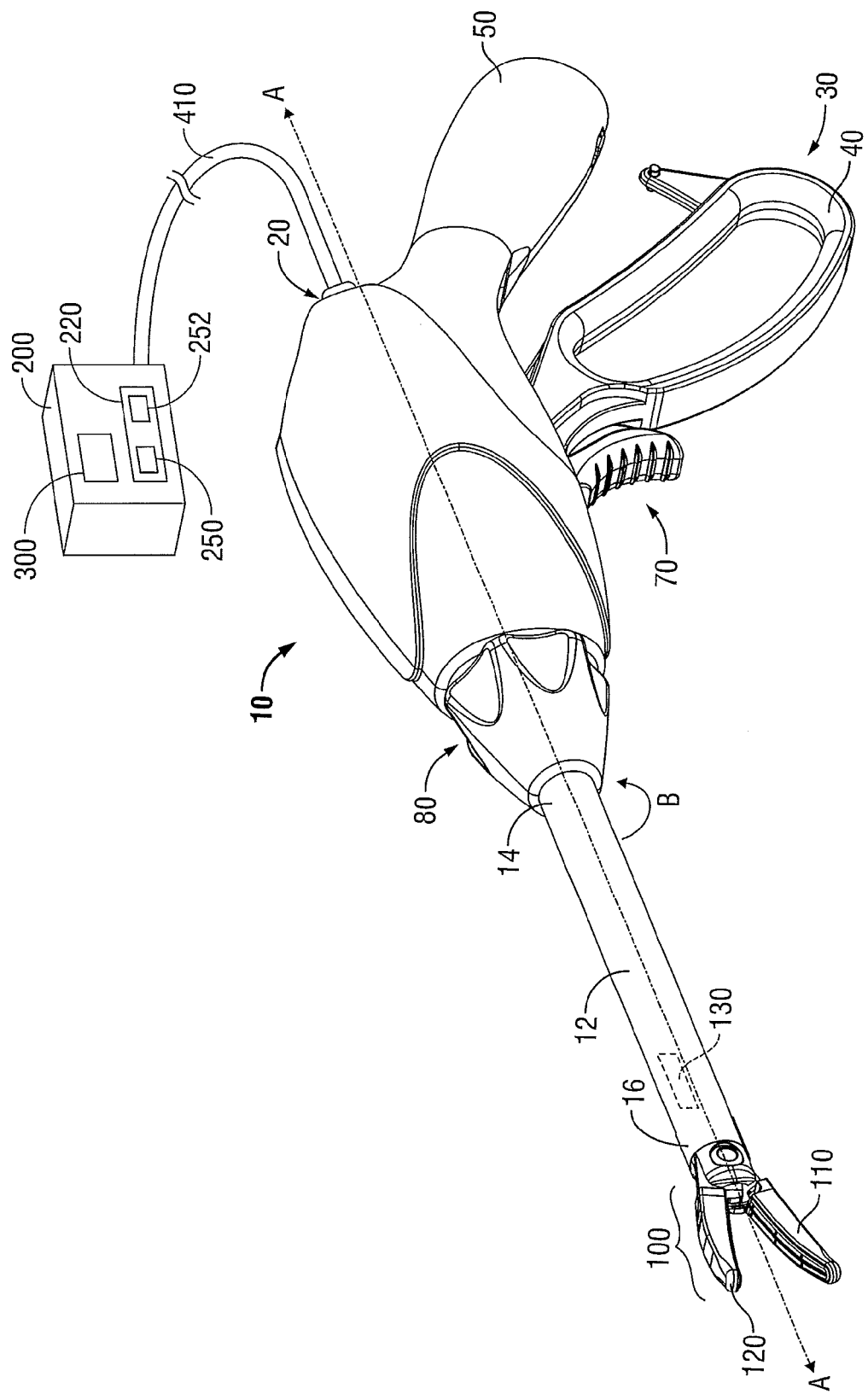
FIG. 1 is a perspective view of an electrosurgical apparatus and electrosurgical generator according to an embodiment of the present disclosure.

With reference to FIG. 1 an illustrative embodiment of an electrosurgical generator 200 (generator 200) is shown. Generator 200 operatively and selectively connects to an endoscopic or laparoscopic forceps (e.g., bipolar forceps 10) for performing an electrosurgical procedure. As noted above, an electrosurgical procedure may include sealing, cutting, cauterizing coagulating, desiccating, and fulgurating tissue; all of which may employ RF energy. Generator 200 may be configured for monopolar and/or bipolar modes of operation. Generator 200 includes all suitable components, parts, and/or members needed for a control system 300 (system 300) to function as intended. Generator 200 generates electrosurgical energy, which may be RF (radio frequency), microwave, ultrasound, infrared, ultraviolet, laser, thermal energy or other suitable electrosurgical energy.

An electrosurgical module 220 generates RF energy and includes a power supply 250 for generating energy and an output stage 252, which modulates the energy that is provided to the delivery device(s), such as the end effector assembly 100, for delivery of the modulated energy to a patient. Power supply 250 may be a high voltage DC or AC power supply for producing electrosurgical current, where control signals generated by the system 300 adjust parameters of the voltage and current output, such as magnitude and frequency. The output stage 252 may modulate the output energy (e.g., via a waveform generator) based on signals generated by the system 300 to adjust waveform parameters, e.g., waveform shape, pulse width, duty cycle, crest factor, and/or repetition rate. System 300 may be coupled to the generator module 220 by connections that may include wired and/or wireless connections for providing the control signals to the generator module 220.

With reference again to FIG. 1, the electrosurgical apparatus can be any suitable type of electrosurgical apparatus, including but not limited to electrosurgical apparatuses that can grasp and/or perform any of the above mentioned electrosurgical procedures. As noted above, one type of electrosurgical apparatus may include bipolar forceps 10 as disclosed in United States Patent Publication No. 2007/0173814 entitled "Vessel Sealer and Divider For Large Tissue Structures". A brief discussion of bipolar forceps 10 and components, parts, and members associated therewith is included herein to provide further detail and to aid in the understanding of the present disclosure.

With continued reference to FIG. 1, bipolar forceps 10 is shown for use with various electrosurgical procedures and generally includes a housing 20, a handle assembly 30 that includes a movable handle 40 and a fixed handle 50, a rotating assembly 80, a trigger assembly 70, a shaft 12, a drive assembly 130, and an end effector assembly 100, which mutually cooperate to grasp, seal and/or divide large tubular vessels and large vascular tissues. Although the majority of the figure drawings depict a bipolar forceps 10 for use in connection with endoscopic or laparoscopic surgical procedures, the present disclosure may be used for more traditional open surgical procedures.

Shaft 12 has a distal end 16 dimensioned to mechanically engage the end effector assembly 100 and a proximal end 14 which mechanically engages the housing 20. In the drawings and in the descriptions that follow, the term "proximal," as is traditional, will refer to the end of the forceps 10 that is closer to the user, while the term "distal" will refer to the end that is farther from the user.

Figure 2:
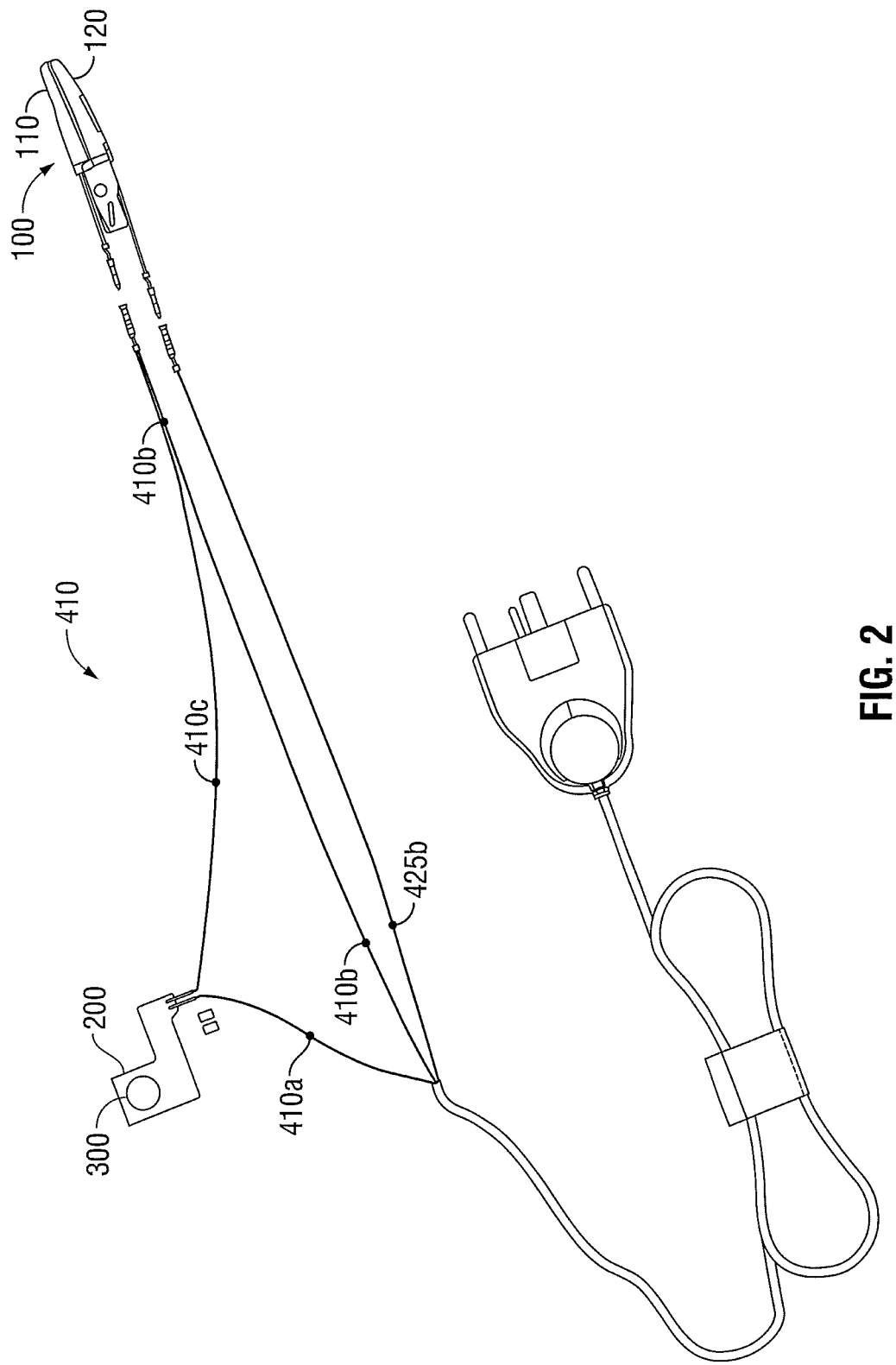
FIG. 2 is a schematic representation of an electrical configuration for connecting the electrosurgical apparatus to the electrosurgical generator depicted in FIG. 1.

Forceps 10 includes an electrosurgical cable 410 that connects the forceps 10 to a source of electrosurgical energy, e.g., generator 200, shown schematically in FIG. 1. As shown in FIG. 2, cable 410 is internally divided into cable leads 410a, 410b, 410c, and 425b which are designed to transmit electrical potentials through their respective feed paths through the forceps 10 to the end effector assembly 100.

For a more detailed description of shaft 12, trigger assembly 70, rotating assembly 80 and electrosurgical cable 410 (including line-feed configurations and/or connections) reference is made to commonly owned Patent Publication No., 2003-0229344, filed on Feb. 20, 2003, entitled "VESSEL SEALER AND DIVIDER AND METHOD OF MANUFACTURING THE SAME."

With reference again to FIG. 1, movable handle 40 includes an aperture configured for receiving one or more of an operator's fingers to enhance movement of the handle 40. Movable handle 40 is in operative communication with generator 200 including system 300, end effector assembly 100 and/or drive assembly 130. Movable handle 40 is selectively movable from a first position relative to a fixed handle 50 to a second position in closer proximity to the fixed handle 50 to close jaw members 110 and 120. The internal electrically and/or mechanically cooperating components associated with the movable handle 40 to impart movement of the jaw members 110, 120 of end effector assembly 100 is commonly known and may include any number of electrical connections, configurations and/or components (e.g., resistors, capacitors, inductors, rheostats, etc.), and gears, links, springs, and/or rods such that forceps 10 may function as intended.

Fixed handle 50 provides a gripping surface for an operator's hand such that an operator may effectively manipulate the forceps 10 internal or external a patient.

Figure 3:
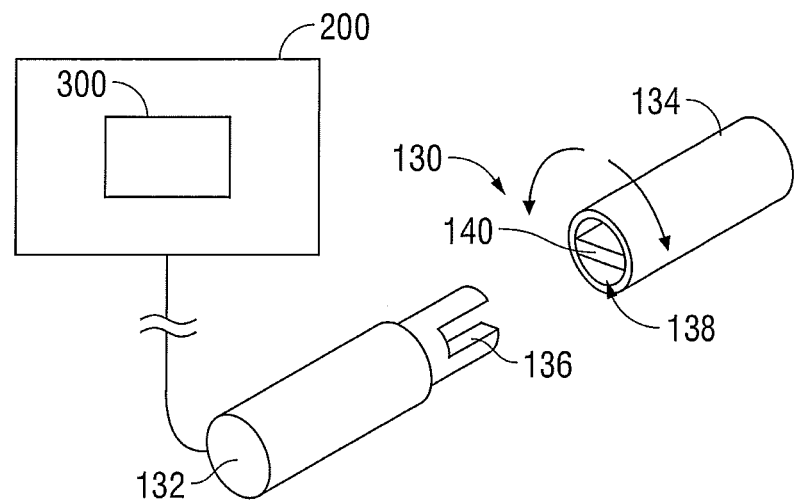
FIG. 3 is an enlarged, side perspective view of a drive assembly suitable for use with the end effector assembly of FIG. 1.

With reference now to FIG. 3, drive assembly 130 is shown. As noted above, drive assembly 130 operatively connects to movable handle 40 such that an operator may impart movement of the jaw members 110, 120. With this purpose in mind, drive assembly 130 may include any number of electrical connections, configurations and/or components (e.g., resistors, capacitors, inductors, rheostats, etc.), and gears, links, springs, and/or rods such that forceps 10 may function as intended. In an embodiment, drive assembly includes a solenoid 132 and a drive rod 134 that operatively couples to one or both of the jaw members 110, 120. While drive assembly 130 is shown including solenoid 132, other electromechanical and/or mechanical devices may be included and/or employed with the drive assembly 130 of the present disclosure, such as, for example, transducers, relays, and the like.

Solenoid 132 may be operatively supported at a distal end of shaft 12 and operatively disposed relative to end effector 100 and/or jaw members 110, 120, such that movement of solenoid 132 causes movement of the jaw members 110, 120. Solenoid 132 serves to convert energy (e.g., electrosurgical energy in the form of an actuation signal) into linear motion, rotational motion, or combination thereof, such that jaw members 110, 120 may move from an opened to closed configuration such that tissue may be grasped therebetween. Solenoid 132 operatively communicates with generator 200 and may include any number of contacts and/or leads. For example, solenoid 132 may include one or more contacts (not explicitly shown) that operatively couple to cable 410. In an embodiment, solenoid 132 may includes a clevis 136 and/or other suitable structure located at a distal end thereof that operatively connects to drive rod 134.

With continued reference to FIG. 3, drive rod 134 is shown. Drive rod 134 is configured to operatively couple to one or both of the jaw members 110, 120 such that one or both of the jaw members 110, 120 is/are moveable from an open configuration to a closed configuration. To this end, drive rod 134 communicates the linear and/or rotational motion produced by solenoid 132 to one or both of the jaw members 110, 120. In an embodiment, drive rod 134 may include and/or define a bore or opening 138, or other suitable structure(s) that couples to clevis 136 of solenoid 132. As shown, opening 138 is defined by drive rod 134 and is generally circumferential in shape and includes a bar or other suitable structure 140 that is configured to engage clevis 136.

Figure 4:
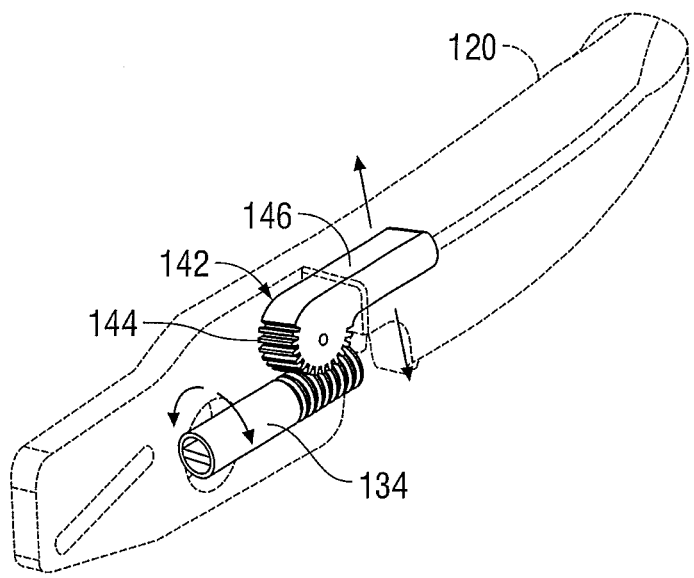
FIG. 4 is an enlarged, side perspective view of a gear configuration suitable for use with the drive assembly of FIG. 4 according to an embodiment of the present disclosure.

Drive rod 134 and one or both of the jaw members 110,120 may be configured to form a worm gear configuration (FIG. 4). This type of gear configuration is known in the art and typically includes one or more teeth and/or screw-type threads that are configured to matingly engage with each other. While the drive assembly 130 of the present disclosure is described in terms of use with the worm gear configuration, other gear configurations are contemplated, such as, for example, spur gear, single and/or double helical gears, bevel gears, crown gears, hypoid gears, etc.

Depending on a specific gear configuration, opening 138 may be configured to impart linear and/or rotational motion of drive rod 134. For example, in an embodiment that employs a worm gear configuration, opening 138 may be located at a proximal end of drive rod 134. In this instance, rotational movement of the solenoid 132 causes a "worm" (e.g., drive rod 134) to rotate, which, in turn, causes a "gear"

(e.g., a gear structure 142 operatively coupled to one or both of the jaw members 110, 120) to rotate and cause one or both of the jaw members 110, 120 to move from an opened to closed configuration. Gear structure 142 includes a proximal end including a plurality of teeth 144 and an elongated distal end 146 configured to operatively couple to one or both of the jaw members 110, 120. For illustrative purposes, gear structure is shown operatively coupled to jaw member 120. As can be appreciated by one of ordinary skill in the art, different gear configurations, which may include more or less of the same, similar, and/or different structures and/or operative connections, may be employed with the drive assembly 130 of the present disclosure.

Figure 5:
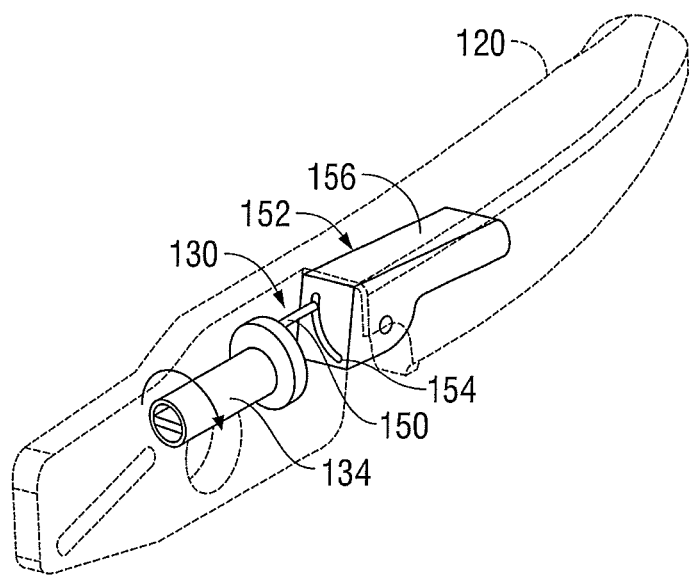
FIG. 5 is an enlarged, side perspective view of an axial cam slot configuration suitable for use with the drive assembly of FIG. 4 according to an embodiment of the present disclosure.

FIG. 5 shows an alternate embodiment of the drive assembly 130. In this instance, the drive rod 134 and one or both of the jaw members 110,120 form an "axial cam-slot" configuration. More particularly, drive rod 134 includes similar structure (e.g., opening 138 and bar 140) as mentioned above and previously described, and includes one or more rotational cam pins 150 located at a distal end thereof that is configured to engage one or more corresponding cam mechanisms 152 operatively coupled to or defined by one or both of the jaw members 110, 120. Cam mechanism 152 includes a proximal end including one or more cam slots 154 configured to engage cam pin 150 and elongated distal end 156 configured to operatively couple to one or both of the jaw members 110, 120. For illustrative purposes, cam slot(s) 154 is shown operatively coupled jaw member 120. In this instance, rotational movement of the solenoid 132 causes cam pin 150 of drive rod 134 to rotate within cam slot 154 on one or both of the jaw members 110, 120, which, in turn, causes one or both of the jaw members 110, 120 to move from an opened to closed configuration. Different camming configurations, which may include more or less of the same, similar, and/or different structures and/or operative connections, may be employed with the drive assembly 130 of the present disclosure.

Figure 6:
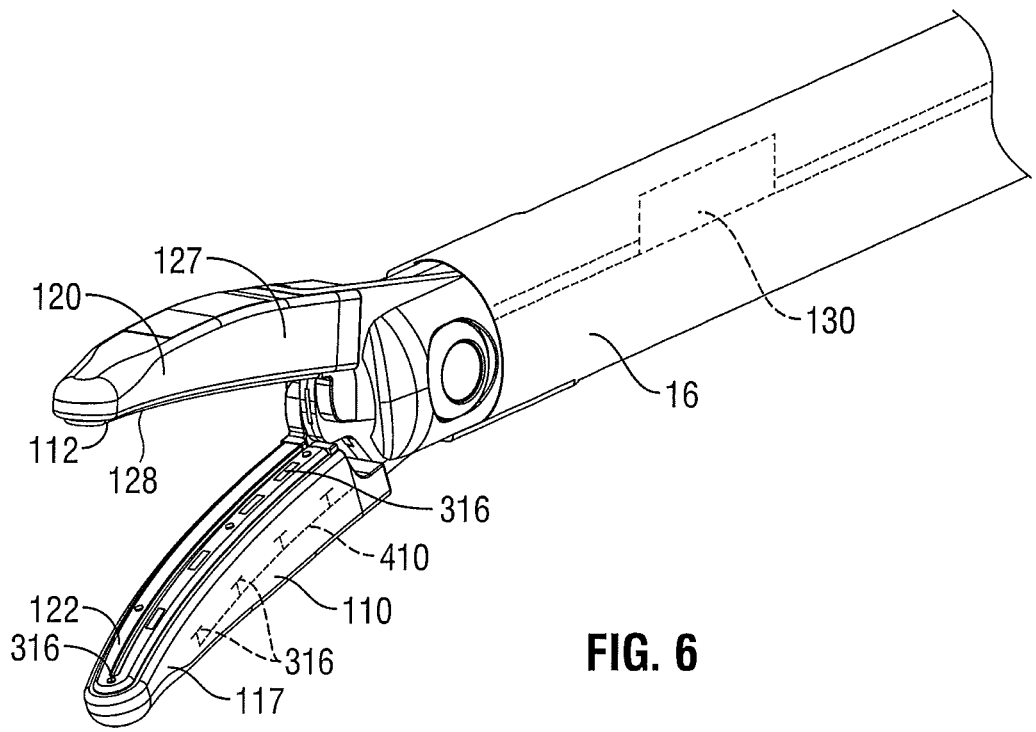
FIG. 6 is an enlarged, side perspective view of the end effector assembly of FIG. 1.

With reference now to FIG. 6 end effector assembly 100 is shown attached at the distal end 16 of shaft 12 and includes a pair of opposing jaw members 110 and 120. As noted above, movable handle 40 of handle assembly 30 operatively couples to drive assembly 130 which, together, electromechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Jaw member 110 includes an insulative jaw housing 117 and an electrically conductive seal plate 118 (seal plate 118). The insulator 117 is configured to securely engage the electrically conductive seal plate 118. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118.

Jaw member 120 includes a similar structure having an outer insulative housing 127 that is overmolded to capture seal plate 128.

As noted above, one or both of the jaw members 110, 120 is/are operatively connected to drive rod 134 of drive assembly 130. In an embodiment, one or both of the jaw members 110, 120 may be operatively connected to one or more gear structures 142 (FIG. 4 illustrates jaw member 120 operatively coupled to gear structure 142) that are configured to mesh with one or more teeth or screw-type threads, such as, for example, those associated with a worm gear configuration. Alternatively, one or both of the jaw members may be operatively coupled to one or more cam mechanism 152 (FIG. 5 illustrates jaw member 120 operatively coupled to cam slot structure 152). In some embodiments, one or both of the jaw members 110, 120, may include openings located at a proximal end thereof and configured to receive one or more of the gear structures 142 and/or cam mechanisms 152.

One or both of the jaw members 110,120 include one or more sensors 316 (FIG. 6). Sensors 316 are placed at predetermined locations on, in, or along surfaces of the jaw members 110, 120. In some embodiments, end effector assembly 100 and/or jaw members 110 and 120 may have sensors 316 placed near a proximal end and/or near a distal end of jaw members 110 and 120, as well as along the length of jaw members 110 and 120.

With reference again to FIG. 1, a system 300 for performing an electrosurgical procedure (e.g., RF tissue procedure) is shown. System 300 is configured to, among other things, analyze parameters such as, for example, power, temperature, pressure, current, voltage, impedance, etc., such that a proper tissue effect can be achieved.

Figure 7:
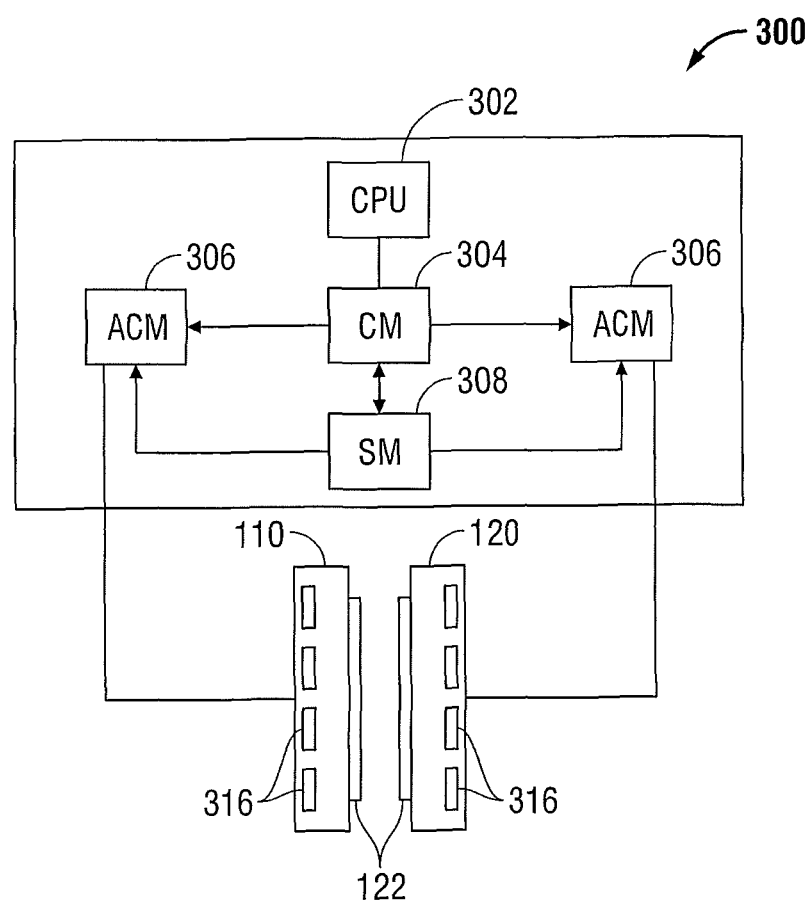
FIG. 7 is a block diagram illustrating components of a control system configured for use with the electrosurgical apparatus and electrosurgical generator of FIG. 1.

With reference now to FIG. 7, system 300 includes one or more processors 302 in operative communication with a control module 304 executable on the processor 302, and may be configured to quantify one or more various parameters (e.g., electrical and/or mechanical parameters associated with bipolar forceps 10) such that a consistent and effective tissue effect may be achieved. Control module 304 instructs one or more modules to transmit electrosurgical energy, which may be in the form of a wave or signal/pulse, via one or more cables (e.g., cable 410) to one or both seal plates 118, 128 and/or an electromechanical drive assembly 130 (drive assembly 130). Control module 304 may instruct an actuation control module 306 (ACM 306) to transmit electrosurgical energy in the form of an actuation signal, via one or more cables (e.g., cable 410) to drive assembly 130.

The control module 304 processes information and/or signals (e.g., pressure data from sensors 316) input to the processor 302 and generates control signals for modulating the electrosurgical energy in accordance with the input information and/or signals. Information may include pre-surgical data (e.g., pressure threshold values) entered prior to the electrosurgical procedure or information entered and/or obtained during the electrosurgical procedure through one or more modules (e.g., ACM 306) and/or other suitable device(s). The information may include requests, instructions, ideal mapping(s) (e.g., look-up-tables, continuous mappings, etc.), sensed information and/or mode selection.

The control module 304 regulates the generator 200 (e.g., the power supply 250 and/or the output stage 252) which adjusts various parameters (e.g., voltage, current, resistance, etc.). Control module 304 may also regulate the electrosurgical energy delivered to the patient (via one or both of the seal plates) and/or to the drive assembly 130 during the electrosurgical procedure.

The control module 304 includes software instructions executable by the processor 302 for processing algorithms and/or data received by sensors 316, and for outputting control signals to the generator module 220 and/or other modules. The software instructions may be stored in a storage medium such as a memory internal to the processor 302 and/or a memory accessible by the processor 302, such as an external memory, e.g., an external hard drive, floppy diskette, CD-ROM, etc.

In some embodiments, an audio or visual feedback monitor or indicator (not explicitly shown) may be employed to convey information to the surgeon regarding the status of a component of the electrosurgical system or the electrosurgical procedure (e.g., pressure exerted by the jaw members on tissue grasped therebetween). Control signals provided to the generator module 220 are determined by processing (e.g., performing algorithms), which may include using information and/or signals provided by sensors 316.

The control module 304 regulates the electrosurgical energy in response to feedback information (e.g., information related to tissue condition at or proximate the surgical site and/or information related to jaw operation). Processing of the feedback information may include determining: changes in the feedback information; rate of change of the feedback information; and/or relativity of the feedback information to corresponding values sensed prior to starting the procedure (pre-surgical values) in accordance with the mode, control variable(s) and ideal curve(s) selected. The control module 304 then sends control signals to the generator module 220 such as for regulating the power supply 250 and/or the output stage 252.

Regulation of certain parameters of the electrosurgical energy may be based on a tissue response such as recognition of when a proper seal is achieved and/or when a predetermined threshold temperature value is achieved. Recognition of the event may automatically switch the generator 200 to a different mode of operation and subsequently switch the generator 200 back to an original mode after the event has occurred. In embodiments, recognition of the event may automatically switch the generator 200 to a different mode of operation and subsequently shutoff the generator 200.

ACM 306 (shown as two modules for illustrative purposes) may be digital and/or analog circuitry that can receive instructions from and provide status to a processor 302 (via, for example, a digital-to-analog or analog-to-digital converter). ACM 306 is also coupled to control module 304 to receive one or more electrosurgical energy waves at a frequency and amplitude specified by the processor 302, and/or transmit the electrosurgical energy waves along the cable 410 to one or both of the seal plates 118, 128, drive assembly 130, and/or sensors 316. ACM 306 can also amplify, filter, and digitally sample return signals received by sensors 316 and transmitted along cable 410.

A sensor module 308 senses electromagnetic, electrical, and/or physical parameters or properties at the operating site and communicates with the control module 304 and/or ACM 306 to regulate the output electrosurgical energy. The sensor module 308 may be configured to measure, e.g., "sense", various electromagnetic, electrical, physical, and/or electromechanical conditions, such as at or proximate the operating site, including: tissue impedance, tissue temperature, tissue pressure (i.e., pressure exerted by the jaw members on tissue), and so on. For example, sensors of the sensor module 308 may include sensors 316 and/or other suitable sensor(s), such as, for example, optical sensor(s), proximity sensor(s), tissue moisture sensor(s), temperature sensor(s), and/or real-time and RMS current and voltage sensing systems. The sensor module 308 measures one or more of these conditions continuously or in real-time such that the control module 304 can continually modulate the electrosurgical output in real-time.

In some embodiments, sensors 316 may include a smart sensor assembly (e.g., a smart sensor, smart circuit, computer, and/or feedback loop, etc. (not explicitly shown)). For example, the smart sensor may include a feedback loop which indicates when a tissue seal is complete based upon one or more of the following parameters: tissue temperature, tissue pressure, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal.

Operation of bipolar forceps 10 under the control of system 300 is now described. Initially the jaw members 110, 120 are in an open configuration and tissue is positioned therebetween. An operator squeezes movable handle 40 in a direction toward fixed handle 50. Processor 302 instructs ACM 306 to generate electrosurgical energy (e.g., in the form of an actuation signal) in response to the processor instructions. The ACM 306 can access a pulse rate frequency clock associated with a time source (not explicitly shown) to form an electrosurgical pulse/signal (e.g., actuation signal) exhibiting the attributes (e.g., amplitude and frequency) specified by the processor 302 and can transmit such pulse/signal on one or more cables (e.g., cable 410) to drive assembly 130, sensors 316, and/or one or more contacts (not explicitly shown) of solenoid 132. In another embodiment, the processor does not specify attributes of the electrosurgical pulse/signal, but rather instructs/triggers other circuitry to form the electrosurgical pulse/signal and/or performs timing measurements on signals conditioned and/or filtered by other circuitry.

Solenoid 132 converts a portion of the electrosurgical energy of the actuation signal to rotational motion, which, in turn, causes rotation of drive rod 134 of drive assembly 130. Rotation of drive rod 134 imparts movement on one or both of the jaw members 110, 120 such that tissue may be grasped therebetween.

Data, such as, for example, pressure, temperature, impedance and so forth is sensed by sensors 316 and transmitted to and sampled by the ACM 306 and/or sensor module 308.

The data can be processed by the processor 302 and/or ACM 306 to determine, for example, when a threshold pressure (e.g., pressure exerted on tissue by the jaw members 110, 120) value has been achieved. The processor 302 can subsequently transmit and/or otherwise communicate the data to the control module 304 such that output power from generator 200 may be adjusted accordingly. The processor 302 can also subsequently transmit and/or otherwise communicate the data to a local digital data processing device, a remote digital data processing device, an LED display, a computer program, and/or to any other type of entity (none of which being explicitly shown) capable of receiving the such data.

Upon reaching a desired threshold pressure, processor 302 instructs control module 304 to generate electrosurgical energy in response to the processor instructions, to one or more of the seal plates 118, 128 such that a desired tissue effect maybe achieved (e.g., tissue seal).

Once the desired tissue effect has been achieved an operator may release moveable handle 40, which, in turn, causes the jaw members 110, 120 to return to their initial open configuration.

From the foregoing and with reference to the various figure drawings, those skilled in the art will appreciate that certain modifications can also be made to the present disclosure without departing from the scope of the same. For example, instead of employing a drive assembly 130, a solenoid 132 may be directly connected to one or both of the jaw members and configured for imparting movement of one or both of the jaw members. Additionally, solenoid 132 may be in the form of a "pancake motor" and may disposed adjacent to or coupled to a pivot associated with the jaw members 110, 120.

Figure 8:
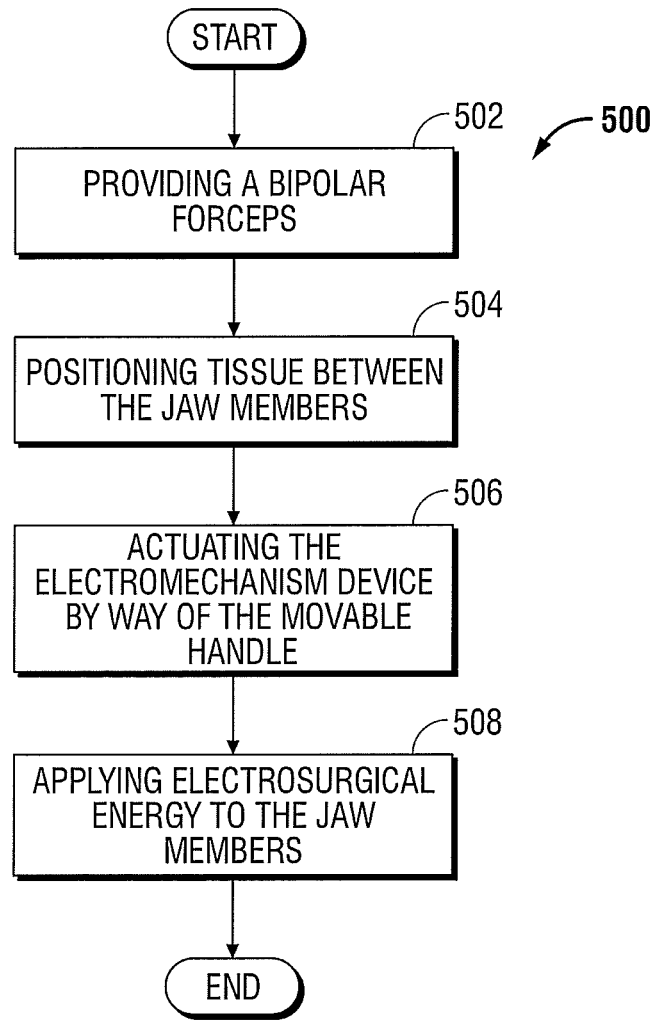
FIG. 8 is a flowchart of a method for performing an electrosurgical procedure according to an embodiment of the present disclosure.

FIG. 8 shows a method 500 for performing an electrosurgical procedure. At step 502, an electrosurgical apparatus e.g. forceps 10 including a pair of jaw members 110, 120 configured to grasp tissue therebetween is provided. At step 504, tissue is positioned between the jaw members 110, 120. At step 506, the electromechanical apparatus is actuated. And at step 508, electrosurgical energy is applied to the jaw members 110, 120 such that a tissue seal may be effected therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
  a housing having a movable handle and a shaft that extend therefrom;
  a solenoid in operative communication with the movable handle and operatively coupled to a drive rod that extends through the shaft; and
  an end effector assembly operably coupled to a distal end of the shaft and including a pair of first and second jaw members, at least one of the first and second jaw members operably coupled to the drive rod for imparting movement thereof from an open configuration to a closed configuration to grasp tissue,
  wherein the drive rod includes at least one cam pin at a distal end thereof configured to engage a corresponding cam slot on the at least one moveable jaw member such that rotation of the solenoid imparts rotational movement of the drive rod to move the at least one movable jaw member between the open configuration and closed configuration.

2. The electrosurgical forceps according to claim 1, wherein the corresponding cam slot of the at least one movable jaw member is located at a proximal end of thereof.

3. The electrosurgical forceps according to claim 1, wherein the solenoid is housed within the at least one movable jaw member.

4. The electrosurgical forceps according to claim 1, wherein the solenoid includes a protrusion at a distal end thereof that is configured to engage a corresponding opening defined in the drive rod.

5. The electrosurgical forceps according to claim 1, wherein the electrosurgical forceps is in operative communication with a control system that sends an actuation signal to the solenoid for driving the drive rod.

6. A method for performing an electrosurgical procedure, the method comprising:
  providing an electrosurgical forceps including:
    a housing having a movable handle and a shaft that extend therefrom;
    a solenoid in operative communication with the movable handle and operatively coupled to a drive rod that extends through the shaft;
    an end effector assembly operably coupled to a distal end of the shaft and including a pair of first and second jaw members, at least one of the first and second jaw members operably coupled to the drive rod for imparting movement thereof from an open configuration to a closed configuration to grasp tissue;
    at least one cam pin at a distal end of the drive rod configured to engage a corresponding cam slot on the at least one moveable jaw member such that rotation of the solenoid imparts rotational movement of the drive rod to move the at least one movable jaw member between the open configuration and closed configuration;

positioning tissue between the pair of first and second jaw members;

actuating the solenoid via the movable handle to move the drive rod to cause the jaw members to move to the closed configuration to grasp tissue; and applying electrosurgical energy to the first and second jaw members such that a tissue seal may be effected therebetween.

7. The method according to claim 6, wherein the step of actuating further comprises measuring a pressure exerted on tissue by the jaw members.

8. The method according to claim 6, further comprising independently controlling and monitoring the delivery of electrosurgical energy.

9. A system for performing an electrosurgical procedure comprising:

an electrosurgical forceps including:

a housing having a movable handle and a shaft that extend therefrom;

a solenoid in operative communication with the movable handle and operatively coupled to a drive rod that extends through the shaft; and an end effector assembly operably coupled to a distal end of the shaft and including a pair of first and second jaw members, at least one of the first and second jaw members operably coupled to the drive rod for imparting movement thereof from an open configuration to a closed configuration to grasp tissue, wherein the drive rod includes at least one cam pin at a distal end thereof configured to engage a corresponding cam slot on the at least one moveable jaw member such that rotation of the solenoid imparts rotational movement of the drive rod to move the at least one movable jaw member between the open configuration and closed configuration; and wherein the electrosurgical apparatus is in operative communication with a control system having at least one algorithm for at least one of independently controlling and monitoring the delivery of electrosurgical energy from the source of electrosurgical energy to the solenoid and the tissue sealing plate on each of the first and second jaw members.

\* \* \* \* \*